United States Patent [19]
Basaj et al.

[11] Patent Number: 5,681,269
[45] Date of Patent: Oct. 28, 1997

[54] JOINT EXTENSION SPLINT

[75] Inventors: Barbara L. Basaj; Carl E. Krippendorf, both of Milwalkee, Wis.

[73] Assignee: Smith & Nephew Rolyan Inc., Germantown, Wis.

[21] Appl. No.: 572,207

[22] Filed: Dec. 13, 1995

[51] Int. Cl.[6] ................................. A61F 5/04; A61F 5/00
[52] U.S. Cl. ................................ 602/22; 602/5; 602/21
[58] Field of Search ........................... 602/5, 6, 7, 20–22; 128/877–880; 482/47, 48

[56] References Cited

U.S. PATENT DOCUMENTS

| | | | |
|---|---|---|---|
| 2,237,251 | 4/1941 | Longfellow | 128/87 |
| 3,794,019 | 2/1974 | Ritland et al. | 128/77 |
| 4,441,489 | 4/1984 | Evans | 602/22 |
| 4,944,290 | 7/1990 | Hepburn | 128/87 |
| 4,949,711 | 8/1990 | Gyovai | 602/21 |
| 5,022,389 | 6/1991 | Brennan | 606/204.45 |
| 5,183,458 | 2/1993 | Marx | 602/22 |
| 5,191,903 | 3/1993 | Donohue | 128/879 |
| 5,324,251 | 6/1994 | Watson | 602/16 |
| 5,328,448 | 7/1994 | Gray | 602/22 |
| 5,337,737 | 8/1994 | Rubin et al. | 602/20 |
| 5,376,091 | 12/1994 | Hotchkiss | 602/22 |

FOREIGN PATENT DOCUMENTS 191978  11/1907  Germany ...................................... 602/5

*Primary Examiner*—Richard J. Apley
*Assistant Examiner*—Denise Pothier
*Attorney, Agent, or Firm*—Pravel, Hewitt, Kimball & Krieger

[57] ABSTRACT

An adjustable finger support for the proximal interphalangeal joint of a finger of the human hand including an elongated, hinged support base adapted with means for securely, yet comfortably holding the finger in place throughout the course of treatment. The elongated base is divided at the hinge into respective support sections for the proximal phalangeal portion of the finger and the middle phalangeal portion of the finger. Jacking mean, such as a screw jack in the form of an elongated set screw operates in conjunction with hinged attachments to the respective undersides of the proximal and middle interphalangeal support sections to 1) maintain the set position of the angle of the respective base portions and 2) to provide firm, controllable extension of the joint over a wide range by selective operation of the jacking means.

11 Claims, 3 Drawing Sheets

JOINT EXTENSION SPLINT

BACKGROUND OF THE INVENTION

1. Field of the Invention

This invention relates to the medical arts and particularly to splinting devices applicable to the hand to correct disfunction and/or nonfunction of a finger joint due to injury, surgery, deformity or other affliction. The invention particularly relates to devices for extension of a contracted proximal interphalangeal joint of a finger of a human hand, and particularly for treatment of more severe contracture of the proximal interphalangeal joints.

2. Description of the Prior Art

Finger joints may become contracted from a variety of occurrences including injury, surgery, aging or disease affecting the tendons and joint capsule structure. Among the prior approaches to effect a straightening of an afflicted finger/joint was the application of a straight splint to the volar, or palm side of the finger, including a strap or cinch placed over the finger at the afflicted joint and tightening of the strap to draw the joint downwardly toward the splint. One version of such a splint included a raised portion at the distal end of the splint so that the joint could be hyperextended slightly past the fully extended plane so that any remaining elasticity of the tendon, when unleashed, would draw the finger back to a straight extension. Such a device is illustrated in U.S. Pat. No. 3,794,019 to Ritland, et at. A disadvantage to this style of splint lies in the concentration of force directly on the top of the afflicted joint and at the proximal and distal ends of the finger causing tissue breakdown and pain attributed to concentration of forces at three concentrated locations.

An alternative approach to splinting a contracted finger joint involved tensioning of the finger through an elastic or spring movement, which tended to pull the finger against the contraction. Commonly, as the extension of the finger/joint progressed, the prime mover (spring or elastic band) would approach the extent of its throw and the force applied for extension would diminish. This sort of device would thus become less effective as the objective of the treatment was approached and the complete corrective extension was not accomplished. An illustration of a spring powered splint is illustrated and described in U.S. Pat. No. 4,944,290 issued to Hepburn. While effective in treating minor contraction of a finger joint, this apparatus is ineffective in treating severe joint contractions, particularly those where there is severe contracture of the tendons or joint condition causing the contracture to require substantial force to effect the straightening.

A further device for correcting flexion problems of the proximal interphalangeal joint of a finger is disclosed in U.S. Pat. No. 5,324,251 to Watson. The title of the patented invention is Device for Flexing or Straightening a Joint, however other than a single reference to placement of one of the pads of the device, no means are illustrated or described for the straightening of a joint. Irrespectively, the device illustrated provides a band for mounting a support plate transcending the width of the hand adjacent the metacarpophalangeal joints to which plate one or more cantilever devices are attached for effecting a flexing (closing) action on the finger(s) including the effected joint(s). The device does not anticipate the present invention since there is no disclosure of particular apparatus for providing extension and the correction of contraction of such joints.

U.S. Pat. No. 5,183,458 issued to Marx illustrates a finger support useful in straightening finger joints, and particularly the proximal interphalangeal joint. The disclosed device is formed of a malleable base having strap means disposed adjacent one end of the base for holding the afflicted finger against the base. At the other end of the base, beyond the joint to be treated, the underside of the base is adapted with an angular support having disposed therein a set screw operable to vary the angle of a bend introduced into the base when the support is applied by the health care professional. The set screw is selectively turned during the course of treatment so that the finger may be incrementally brought to the extended position by means of the set screw driving the angled base back to the flat condition. As may be appreciated by, examining the structure of the illustrated support, the device is capable only of treating limited degrees of contracture as well as those only requiring nominal applications of a sustained force for extension. As distinctly pointed out in other portions of this specification, the present invention is directed to providing an extension splint capable of treading a wide range of interphalangeal joint contractions, and particularly those having a higher degree of contracture and those requiring greater than normal forces to accomplish extension.

SUMMARY OF THE INVENTION

In accordance with the invention claimed herein, there is disclosed an adjustable finger support for the proximal interphalangeal joint of a finger of the human hand wherein an elongated, hinged support base is adapted with means for securely, yet comfortably holding the finger in place throughout the course of treatment. The elongated base is divided at the hinge into respective support sections for the proximal phalanx portion of the finger and the middle phalanx portion of the finger. Jacking mean, such as a screw jack in the form of an elongated set screw operates in conjunction with hinged attachments to the respective undersides of the proximal and middle interphalangeal support sections to 1) maintain the set position of the angle of the respective base portions and 2) to provide firm, controllable extension of the joint over a wide range by selective operation of the jacking means.

In preferred embodiments of the invention, the adjustable support includes strap holding means on each of the support sections so that each of the proximal and middle interphalangeal finger portions may be securely and comfortably secured to the adjustable support.

Further alternative embodiments of the invention include forming the elongated base of a thermoplastic and adaptation of the base at the location of the hinge by scoring or otherwise partially weakening the base material to form an integral hinge. In a preferred embodiment, the scoring includes removal of a portion of the base material in the central section of the base whereby a slot is formed in the base adjacent the joint to be treated permitting the finger joint to intrude into the hinge region and to be treated through a greater range of extension.

Other embodiments of the invention include the formation of the adjustable support of a low temperature thermoplastic material. Such adaption enables the health care professional applying the treatment to the afflicted finger to effectively customize the finger support by making minor adjustments to the form of the respective support sections for more comfortable, secure holding of the finger in the support.

Further objects and advantages of the invention will become apparent from the following description of the preferred and alternative embodiments of the invention.

BRIEF DESCRIPTION OF THE DRAWINGS

The present invention may be more fully understood with reference to the accompanying drawings in which.

DESCRIPTION OF THE PREFERRED EMBODIMENT

Figure 1:
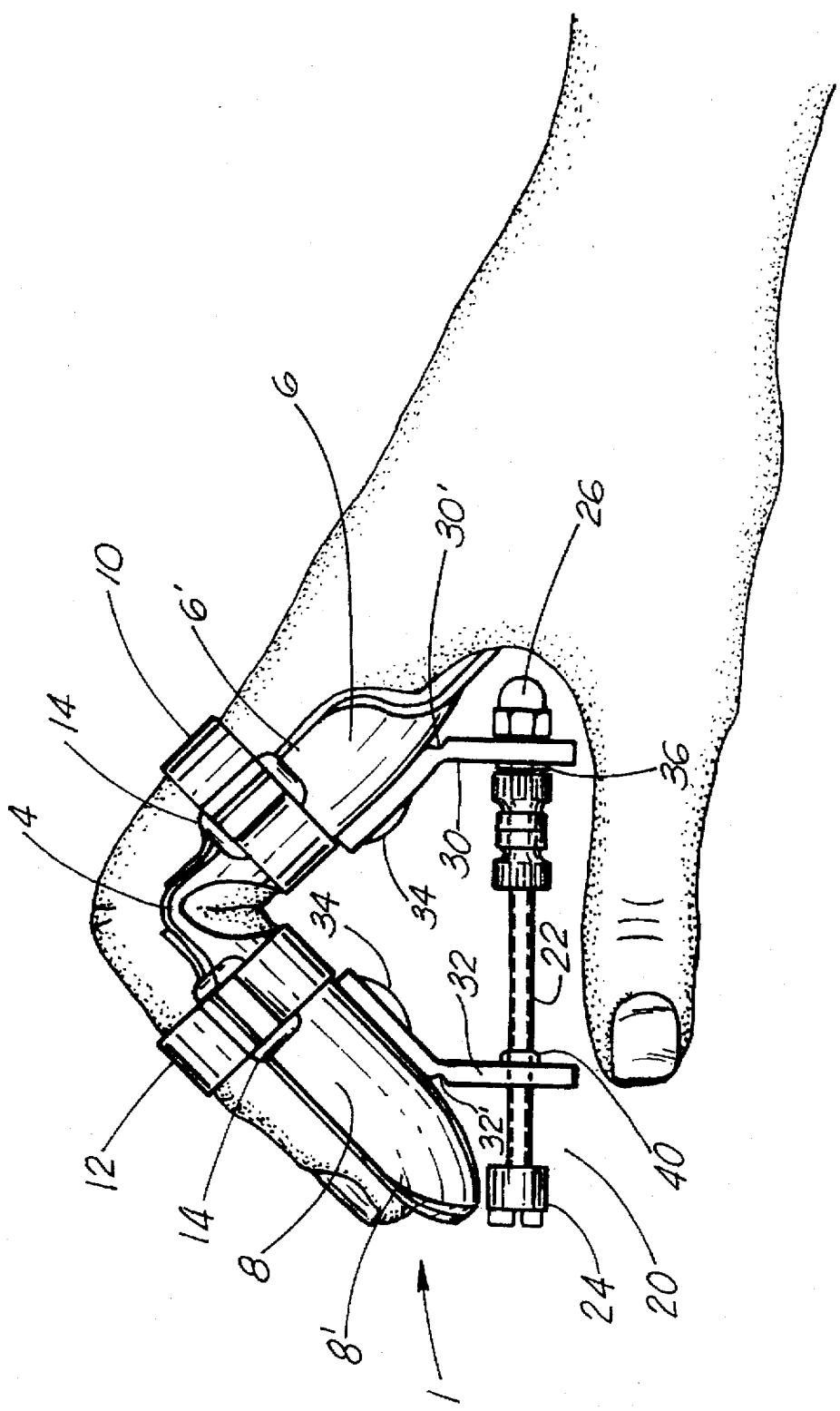
FIG. 1 is a side perspective view of the adjustable finger support, illustrating a finger disposed therein, for use in treatment of contractions of the interphalangeal finger joint.
Figure 2:
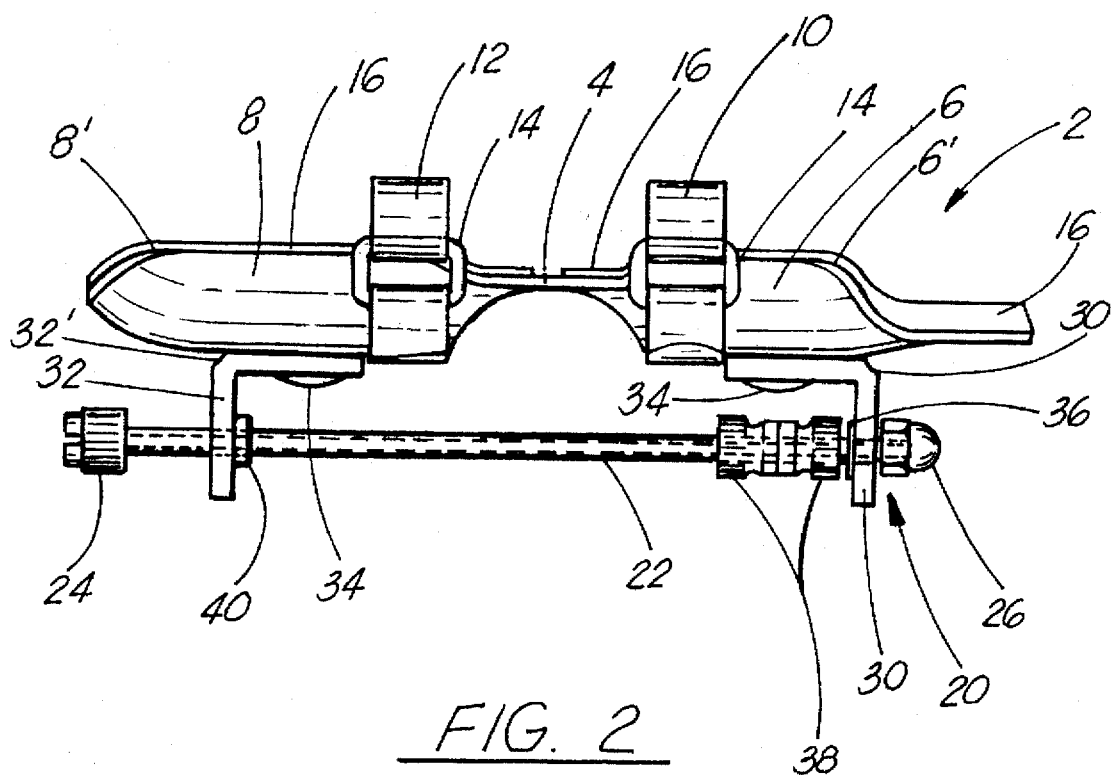
FIG. 2 is a side elevational view of the finger support of FIG. 1.
Figure 4:
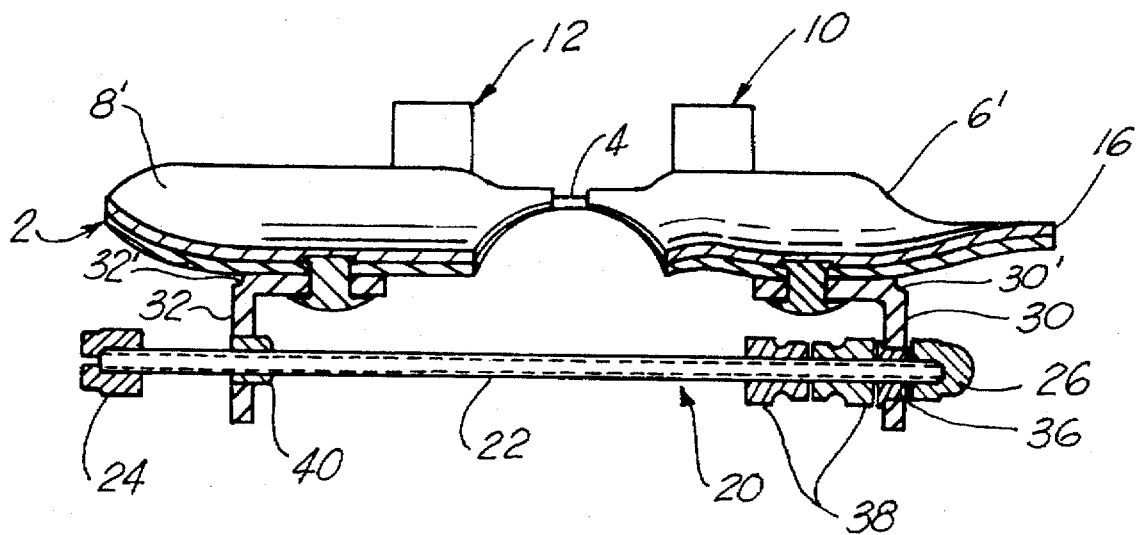
FIG. 4 is a side sectional view taken along line IV—IV of the finger support illustrated in FIG. 3.
Figure 3:
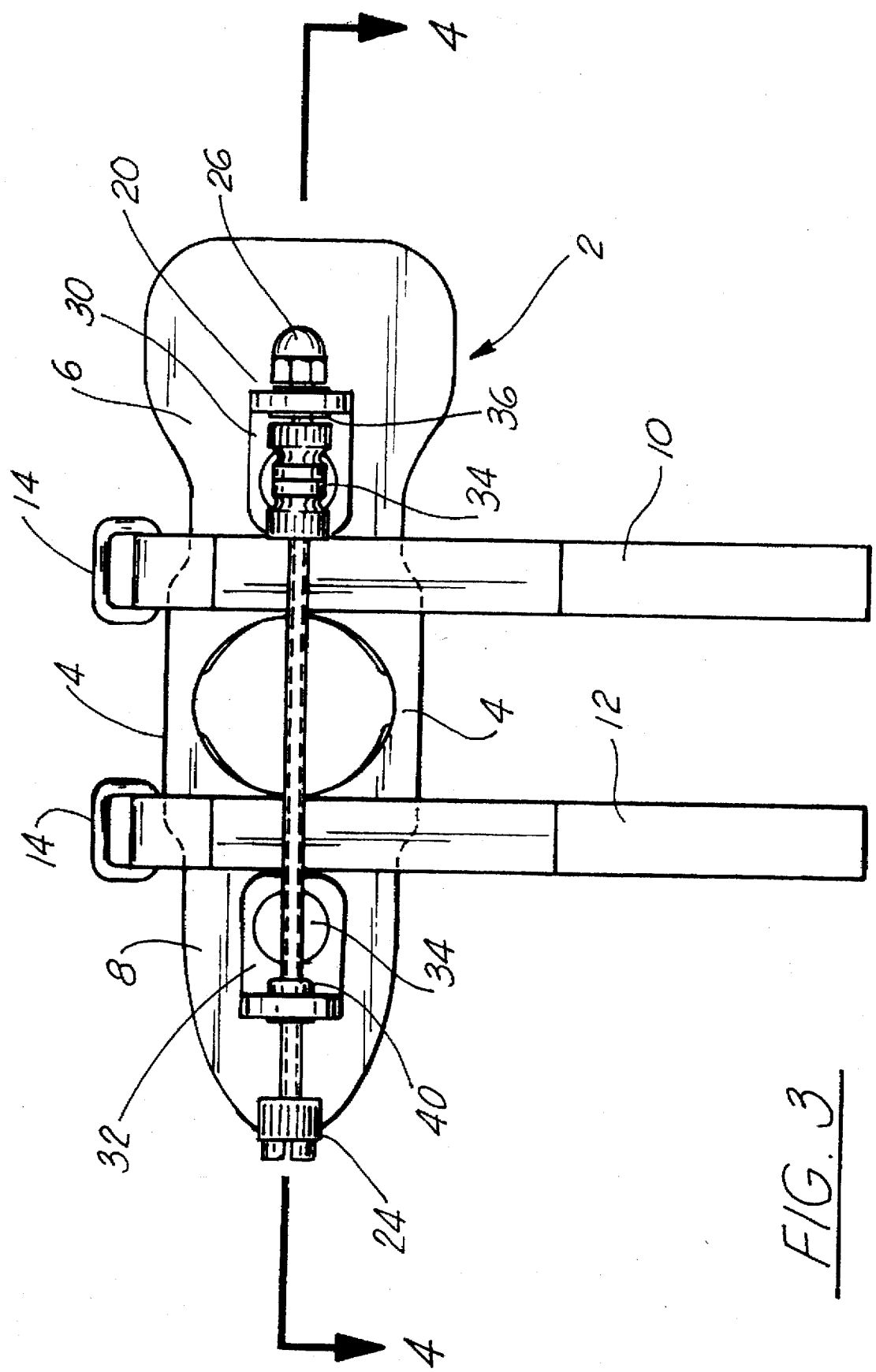
FIG. 3 is a bottom view of the finger support of FIG. 1.

Referring now to the drawings, and in FIGS. 1–3 in particular, the present invention is illustrated in one of the preferred embodiments. The adjustable finger support 1 for treatment of contracted interphalangeal joints of the fingers includes an elongated base 2 having hinge means 4 disposed intermediate support sections 6 and 8 for the proximal phalangeal portion of the finger and the middle phalangeal portion of the finger, respectively. A further preferred embodiment of the invention includes the middle phalangeal portion 8 extended so as to also accommodate the distal phalangeal portion of the finger. By such extension of phalangeal portion 8, the supporting forces are spread over a wider area thereby lessening the likelihood of tissue break-down or discomfort. Disposed on each of the proximal and middle support sections are holding means such as straps 10 (proximal section) and 12 (middle section) for holding the afflicted finger firmly, yet comfortably ha the adjustable support 1.

In the illustrated embodiment holding straps 10 and 12 are illustrated on each of the support portions 6 and 8 since this is preferred. It is considered essential to the invention that only the proximal holding means 6 is essential for effective treatment of an afflicted proximal interphalangeal joint. Holding straps 10 and 12 have "D-rings" 14 disposed at one of their respective ends, to enable quick and secure selective fastening of holding straps 10 and 12 about the afflicted finger, enabling effective treatment for the contracture. Those skilled in the art will recognize that such alternatives as hook and loop fasteners (one type of such is sold under the familiar trademark VELCRO), snap means or hook and eye configurations might also be utilized. In the present embodiment, holding straps 10 and 12 are, as a matter of convenience, retained on their respective phalangeal portions 6 and 8 through the use of an adhesive which may be disposed on either or both of the operative interfaces of holding straps 10 and 12 with phalangeal portions 6 and 8. Suitable alternatives will be recognized by those skilled in the art as including rivet means, hook and loop fastening and similar attachment means.

Each of the proximal and middle portions 6 and 8 preferably include upwardly curved sides, 6' and 8' respectively, to aid in retaining the afflicted finger comfortably and securely in the elongated base 2 for the sequential extension of the proximal interphalangeal joint. It should be recognized that, in the instances of severely contracted joints (up to and including 90° of flexion) substantial forces may be imposed in the extension treatment and retaining the afflicted finger in proper position within the adjustable support 1 is accomplished more effectively and comfortably by supporting the proximal and middle phalangeal portions of the finger over as broad an area as is feasible. Further aiding the distribution of the treatment load in the adjustable support 1 is achieved by the inclusion of padding 16 disposed on the interface of the elongated base 2 interacting with the finger. Those skilled in the art will recognize that adhesive backed foam material, flannel-like material and the like may be conveniently affixed to the phalangeal portions 6 and 8.

Operation of the adjustable support 1 in extension is accomplished through jacking means 20, which in the preferred embodiment includes and elongated set screw 22 having a knurled nut 24 disposed at one of set screw 22 for rotation thereof and a cap nut 26 disposed at the opposite end of set screw 22, conveniently providing a stop for jacking means 20. Jacking means 20 is disposed on elongated base 2 so as to provide articulation of proximal phalangeal portions 6 and 8 about hinge means 4 through jack hinges 30 and 32. Jack hinges 30 and 32 are attached to phalangeal portions 6 and 8 of base 2 by means 34 such as rivets, or other suitable fastening means as is known in the art. In the illustrated embodiment, jack hinge 30 has an eyelet 36 disposed therein through which set screw 22 is rotatably mounted. Set screw 22 is maintained in relative position at jack hinge 30 through the interaction of cap nut 26 and blocking nuts 38 which are set in relative lateral position so that set screw is retained for free movement rotational in eyelet 36 however, is restrained against lateral movement relative to eyelet 36 and hinge 30 only as is required to permit the rotational movement. Those skilled in the art will recognize that alternative means for the mounting of jacking means 20 in jack hinge 30 might be utilized. The illustrated embodiment is particularly useful in that the use of a cap nut 26 and blocking nuts 38 allow for the quick disassembly of the jack means and the utilization of differently sized (lengths) set screws 22 as are convenient for articulation of the adjustable support 1 throughout its broad operable range.

Set screw 22 is disposed in jack hinge 32 by means of a jack nut 40 secured against rotation in jack hinge 32. Jack nut 40 is chosen to have a cooperating bore and internal thread to cooperate with the thread on set screw 22 during rotation of set screw 22. In conventional practice, clockwise rotation of knurled nut 24 will draw jack hinge 32 toward jack hinge 30 causing phalangeal portions 6 and 8 to articulate about hinge means 4. In the usual operation of the adjustable support 1, phalangeal portions 6 and 8 will be articulated to an angle to approximately match the contracture of the afflicted finger such that the adjustable support 1 may be applied to the finger in its contracted condition. Thereafter, set screw is rotated by the health care professional to extend, or move phalangeal portions into and through an obtuse angle toward full extension of the finger. Effecting the treatment will likely be done in successive, sequential rotations of set screw 22, providing incremental, step-wise extension of the finger in amounts tolerable by the patient, and according to the professional judgement of the health care professional.

Particular advantage is achieved in the present invention by fabricating elongated base of a low temperature thermoplastic material. Low temperature thermoplastic materials are those which soften under heat and are capable of being molded and shaped with hand pressure, and subsequently harden retaining the molded shape on cooling without undergoing chemical changes. A low temperature material, suitable for use as an adjustable sprint should soften at sufficiently low temperatures so as to allow for molding directly on the patient without injury due to scalding or burning of the skin. Suitable polymers which melt or soften at temperatures ranging from 50° C. to 100° C. include poly (ethyleneadipate), poly (epsiloncaprolactone), polyvinyl stearate, cellulose acetate, butyrate and ethyl cellulose poly (propylene oxide) containing co-monomers, trans polyisoprene and cis polyisoprene based thermoplastic materials, and polycaprolactone based materials including commercially available polycaprolactone thermoplastic materials known as AQUAPLAST, SYNERGY, EZEFORM, POLYFORM and POLYFLEX II. These thermoplastic materials are available from Smith & Nephew Rolyan Inc., N104, W13400 Donges Bay Road, Germantown Wis. 53022.

A thermoplastic adjustable splint 1 can be made according to the method claimed in U.S. Pat. No. 4,240,415, incorporated herein by reference. This patent describes a thermoplastic material formed from a thermoplastic polyester having a melting point between about 50° C. and 100° C., and more particularly a poly (epsilon-caprolactone) having a weight average molecular weight of over 5,000 with a half time crystallization at 36° C. of between 0.5 and 10 minutes. At room temperature the poly (epsilon-caprolactone) is quite stiff with a 1% secant modulus of 50,000 psi at 23° C. The stiffness remains high as the temperature is increased. At 60° C. some melting occurs and the stiffness modulus is 20,000 psi. Additionally, some of the poly (epsilon-caprolactone) mixtures become transparent when heated which is useful when molding and placing a splinting device on a limb such as a finger. The thermoplastic material also has 100% elastic memory which allows it to be reheated and reshaped repeatedly.

In a preferred embodiment, the thermoplastic material is precut in a shape that conforms to the illustrations in FIGS. 1–3. The thermoplastic material is conveniently formed with the upstanding curved edges 6' and 8' illustrated at FIGS. 1 and 2. The thermoplastic material also facilitates the formation of a particularly useful hinge means 4 and jack hinges 30 and 32. As may be best seen in FIG. 3, however also visible in FIGS. 1 and 2, hinge means 4 is integrally located in base 2, being formed by scoring including thinning or removal of a potion of the base material. In the illustrated embodiment, the formation of hinge means 4 is accomplished by removal of an oval of material from the central portion of base 2, leaving an opening intermediate the two sides of the base 2. With the particular material used for forming base 2, the oval is approximately 1 and a quarter inches in major diameter, and the remaining material on the sides of base 2 at the hinge is about one-eighth inches. As is illustrated in FIG. 1, such an integral hinge means 4 provides room for the flexed proximal interphalangeal joint of the finger to intrude into the hinge means and be more comfortably and securely contained within adjustable support 1. Characteristics of the specific thermoplastic material chosen may require adjustment of the dimensions of the hinge means.

As with hinge means 4, the low temperature thermoplastic material selected for base 2, the same material is particularly useful for forming jack hinges 30 and 32. Such jack hinges 30 and 32 are readily formed by precutting a rectangular piece of thermoplastic material, conveniently one half inches by one and a quarter inches and scoring the material along a laterally extending line intermediate their ends to form the hinge joint 30' and 32'. By reducing the material thickness to approximately one-half its original thickness, an effective hinge is formed. The precut, scored material may then be assembled to the respective phalangeal portions 6 and 8 as illustrated in the figures.

As will be apparent to persons skilled in the art, various additional modifications, adaptations and variations of the foregoing specifically disclosed embodiments can be made without departing form the objectives and scope of the present invention;

Accordingly, we claim:

1. An adjustable finger support for an interphalangeal joint of a human hand for treating contraction of said joint comprising:

an elongate base having a proximal phalangeal base portion and a middle phalangeal base portion for supporting the proximal and middle phalangeal portions of the finger respectively, said elongate base having hinge means disposed intermediate said proximal phalangeal base portion and said middle phalangeal base portion of said elongate base;

said proximal phalangeal base portion and said middle phalangeal base portion form an included angle in said elongate base having said hinge means as the apex of said angle;

holding means disposed on at least said proximal phalangeal base portions for releasably holding said proximal phalangeal portion of said finger securely on said proximal phalangeal base portion;

jack means disposed on the side of said elongate base opposite the finger wherein said jack means is pivotally connected by jack hinge means disposed on said proximal phalangeal base portion and on said middle phalangeal base portion whereby operation of said jack means varies the included angle formed by said elongate base having said hinge means as the apex of said angle;

whereby said contracted finger and joint may be secured in said finger support, wherein said base portions are disposed in angular relationship approximating the angular contraction of said proximal phalangeal base portion and middle phalangeal base portion of said finger and said support may be thereafter selectively articulated by operation of said jack means causing said base portions to angularly rotate lessening said contraction of said proximal interphalangeal joint.

2. The adjustable finger support according to claim 1 wherein said proximal and middle phalangeal base portions have lateral edges upturned from said the plane of said base, forming partially convex cross sections for receiving said proximal and middle phalangeal of said finger therein.

3. The adjustable finger support according to claim 1 wherein operation of said jack means rotates said proximal and middle phalangeal base portions through an obtuse angle.

4. The adjustable finger support according to claim 1 wherein said elongate base is formed of a thermoplastic material.

5. The adjustable finger support according to claim 4 wherein said hinge means is integrally formed in said thermoplastic material by scoring said material.

6. The adjustable finger support according to claim 4 wherein said jack hinge means are formed of a low temperature thermoplastic material.

7. The adjustable finger support according to claim 6 wherein said hinge means in said jack hinge means is formed by scoring said material.

8. The adjustable finger support according to claim 1 wherein said holding means disposed on said proximal phalangeal base portion includes strap means fixedly attached to said base portion on the underside thereof.

9. The adjustable finger support according to claim 1 wherein said holding means is disposed additionally on said middle phalangeal base portion.

10. The adjustable finger support according to claim 9 wherein said middle phalangeal base portion extends to additionally support said distal phalangeal portion of said finger.

11. The adjustable finger support according to claim 1 wherein said jack means is a screw jack operably connected to said elongated base through said jack hinge means.

* * * * *